United States Patent
Levine et al.

(10) Patent No.: US 10,130,099 B2
(45) Date of Patent: Nov. 20, 2018

(54) MODULATION OF PLANT IMMUNE SYSTEM FUNCTION

(71) Applicant: KEMIN INDUSTRIES, INC., Des Moines, IA (US)

(72) Inventors: Robert B. Levine, Ann Arbor, MI (US); Geoffrey P. Horst, Grosse Pointe Farms, MI (US); Jeffrey R. LeBrun, Ann Arbor, MI (US)

(73) Assignee: KEMIN INDUSTRIES, INC., Des Moines, IA (US)

( * ) Notice: Subject to any disclaimer, the term of this patent is extended or adjusted under 35 U.S.C. 154(b) by 0 days.

(21) Appl. No.: 14/210,582

(22) Filed: Mar. 14, 2014

(65) Prior Publication Data

US 2014/0287919 A1  Sep. 25, 2014

Related U.S. Application Data

(60) Provisional application No. 61/782,254, filed on Mar. 14, 2013.

(51) Int. Cl.
*A01N 63/02* (2006.01)
*A01N 43/16* (2006.01)

(52) U.S. Cl.
CPC ............ *A01N 63/02* (2013.01); *A01N 43/16* (2013.01)

(58) Field of Classification Search
None
See application file for complete search history.

(56) References Cited

U.S. PATENT DOCUMENTS

| | | | |
|---|---|---|---|
| 3,873,296 A * | 3/1975 | Ashmead | C05D 9/02 504/190 |
| 5,147,821 A | 9/1992 | McShane et al. | |
| 6,387,847 B1 | 5/2002 | Yvin et al. | |
| 6,939,864 B1 | 9/2005 | Johnson et al. | |
| 2003/0203016 A1 | 10/2003 | Suwelack et al. | |
| 2004/0110638 A1 | 6/2004 | Yvin et al. | |
| 2007/0232494 A1 * | 10/2007 | Briand | A01N 43/16 504/189 |
| 2011/0045015 A1 * | 2/2011 | Berti | A61K 31/716 424/197.11 |
| 2011/0123677 A1 | 5/2011 | Rivera et al. | |
| 2013/0216586 A1 | 8/2013 | LeBrun et al. | |
| 2013/0303752 A1 | 11/2013 | Levine et al. | |

FOREIGN PATENT DOCUMENTS

| | | |
|---|---|---|
| WO | WO-90/12106 A1 | 10/1990 |
| WO | WO-2005/082150 A1 | 9/2005 |
| WO | WO-2007/122264 A2 | 11/2007 |
| WO | WO-2007/122264 A3 | 11/2007 |
| WO | WO-2012/101106 A1 | 8/2012 |
| WO | WO-2014/152174 A1 | 9/2014 |

OTHER PUBLICATIONS

Klarzynski et al. Plant Physiol. vol. 124, pp. 1027-1037. publication year: 2000.*
International Search Report dated Aug. 11, 2014, for PCT Application No. PCT/US2014/027036, filed on Mar. 14, 2014, 2 pages.
Kuda et al., (2009) "Effects of Two Storage β-1,3 Glucans, Laminaran from Eicenia Bicyclis and Paramylon from Euglena Gracili, on Cecal Environment and Plasma Lipid Levels in Rat" Journal of Functional Foods I 399-404.
Written Opinion dated Aug. 11, 2014, for PCT Application No. PCT/US2014/027036, filed on Mar. 14, 2014, 5 pages.
Extended European Search Report dated Aug. 1, 2016, for EP Application No. 14 767 480.8, filed on Mar. 14, 2014, 10 pages.
Marchessault, R.H. et al. (1979). "Fine structure of (1→3)-β-D-glucans: Curdlan and paramylon," *Carbohydrate Research* 75:231-242.
McIntosh, M. et al. (2005). "Curdlan and other bacterial (1→3)-[β]-d-glucans," *Applied Microbiology and Biotechnology* 68(2):163-173.

* cited by examiner

*Primary Examiner* — Katherine Peebles
(74) *Attorney, Agent, or Firm* — Nyemaster Goode P.C.

(57) ABSTRACT

Immune function of a plant can be modulated by administering a composition comprising beta glucan, where the beta glucan includes unbranched beta-(1,3)-glucan. Such unbranched beta-(1,3)-glucan can be obtained from *Euglena*, including heterotrophically grown *Euglena*. The unbranched beta-(1,3)-glucan can be in the form of paramylon and/or can be part of algae meal. The composition can further include a fertilizer, a pesticide, a fungicide, a bactericide, combinations thereof, as well as one or more various plant immune system modulators other than beta glucan. The wellbeing of the plant seed, seedling, mature plant, or harvested plant product can accordingly be improved.

29 Claims, 2 Drawing Sheets

MODULATION OF PLANT IMMUNE SYSTEM FUNCTION

CROSS-REFERENCE TO RELATED APPLICATIONS

This application claims the benefit of U.S. Provisional Application No. 61/782,254, filed on Mar. 14, 2013. The entire disclosure of the above application is hereby incorporated herein by reference.

FIELD

The present technology relates to unbranched beta-(1,3)-glucan, modifications to unbranched beta-(1,3)-glucan, and uses thereof to modulate the immune function of photosynthetic organisms such as terrestrial and aquatic plants, including providing such compositions as foliar sprays and liquid products fed to plants or applied to harvested plant material.

BACKGROUND

This section provides background information related to the present disclosure which is not necessarily prior art.

Cultivation of photosynthetic terrestrial and aquatic plants is a major economic activity throughout the world and provides most people with the majority of their caloric requirements. In addition to agricultural production, many types of photosynthetic terrestrial and aquatic plants, such as flowers, are produced for other uses. Cultivation of these photosynthetic species is often complicated by plant diseases and disorders, which can significantly reduce the productivity of farms. Damage during harvest of crops (e.g., wounds on fruit or tubers) is another time at which disease or disease-causing organisms can negatively impact producers. As a result, farmers use a variety of methods to limit plant disorders and diseases, including chemical treatments, which involve added costs and the potential to damage the environmental, local biodiversity, and the health of farmers and other humans consuming or interacting with the agricultural products. These chemical treatments as well as genetic engineering are widely used to improve the ability of a plant to resist disease and as treatment for a disease, but an over-dependence upon these chemical treatments in modern agriculture has led to widespread resistance and led to a desire for more natural ways to promote healthy immune function in plants.

A plant disorder may be defined as any abnormal plant growth or development. Affected plants do not live up to a grower's normal expectations and are incapable of carrying out normal physiological functions to the best of their genetic potential. Biotic disorders are more typically called plant disease's and are caused by infectious organisms. Some of the most common plant diseases are caused by fungi, bacteria, phytoplasmas, viruses and viroids, nematodes, and parasitic higher plants.

In order for a disease to occur, the host plant must be susceptible to the pathogen or disease organism. Plants and harvested plant material may be susceptible to attack at numerous locations, including the roots, leaves, flowers or the vascular system. In many cases, the host plant must be at a certain physiological state for disease to occur. For example, some pathogenic organisms attack only young plants, others attack mature or aging plants, and some organisms can attack the plant at any growth stage. In most cases, pathogens take advantage of plants that are stressed and have weakened immune systems. Plants are exposed to many stressors that have been shown to affect health, growth, mortality, immune system health, and overall well-being of the plant. Sources of stress can be both biotic, such as crowding, disease, and pests, and abiotic, such as temperature extremes, weather extremes, moisture extremes, light extremes, nutrient extremes, poor soil (e.g., acidity or alkalinity, salt), pesticide toxicity, air pollution, etc.

In general, the term immunity may be defined as the ability of an organism to withstand microbial infection or disease. Plants lack an adaptive immune system like most vertebrates, but have an active innate immune system that is based on the recognition of pathogen-associated molecular patterns (PAMPs). These are conserved molecules that are unique to certain classes of microorganisms. For example, lipopolysaccharides (LPS) derived from Gram-negative bacteria, peptidoglycans from both Gram-positive and gram-negative bacteria, eubacterial flagellin, unmethylated bacterial DNA fragments, as well as fungal cell wall-derived glucans, chitins, mannans and proteins are all capable of triggering the innate immune response. PAMPs are recognized at the plant cell surface through pattern-recognition receptors (PRRs) that trigger numerous responses, some of which can help the plant diminish the effects of disease or microbial invasions.

Although the term PAMPs is used broadly to describe compounds which are recognized by the immune system, PAMPS can also be derived from nonpathogenic or non-disease causing microorganisms. When a PAMP that is nonpathogenic comes into contact with a plant, the plant immune system may become activated as if it was responding to an actual threat, thereby heightening its overall immune response. This may confer greater protection to the plant if an actual disease challenge or pathogenic organism is attacking the plant simultaneously or is likely to attack soon.

Beta glucans are polysaccharides connected by beta glycosidic linkages that can be found in various organisms, such as yeast, mushrooms, kelp, fungi, cereal grains, and others. Although much research has been done on beta glucans used as human dietary supplements or as an animal feed ingredient, the use of beta glucans to promote the immune system health of plants has never been widely commercialized. Most beta glucan products used today are derived from yeast and to a lesser extent from mushrooms, which requires an expensive production process involving extraction of the beta glucan. Existing beta glucan products, as a result of how the beta glucan is produced and its chemical structure, are consequently too expensive to be used on plants. For example, in 2012 the commercial value of such beta glucans was between about 50 to about 100 USD per kg, a price that is commercially prohibitive.

One reason relating to the high cost of beta glucans, is that the beta glucans from yeast are derived from the cell wall of the organism. As such, the resulting beta glucan content of the total biomass used to produce the beta glucan is generally less than ten to fifteen percent. Moreover, the beta glucans contained in an organism's cell wall generally must undergo expensive, multistage extraction processes in order to separate the beta glucan from other cellular materials. Another concern is the chemical composition of the beta glucan. Variations in branching structure, molecular weight, source organism, and method of production and extraction can all affect the efficacy and suitability of different beta glucan products. For example, yeast-derived beta-(1,3/1,6)-glucans comprise the majority of commercial beta glucan products that are intended to stimulate immune system activity. Beta-(1,3/1,4)-glucans from oats have been demonstrated as a useful product for reducing cholesterol, and only these types of beta glucans may be labeled as such according to FDA regulations. Several organisms produce different beta glucan structures and not all beta glucans are equally effective.

SUMMARY

The present technology includes systems, processes, articles of manufacture, and compositions that relate to modulating immune system function of a plant by administering a composition comprising beta glucan to a plant or harvested plant material, where the beta glucan comprises unbranched beta-(1,3)-glucan. Unbranched beta-(1,3)-glucan acts as a PAMP that stimulates the immune system of the plant or harvested plant material, but is derived from a nonpathogenic organism (e.g., Euglena) and can be used to improve the resistance of the plant to infection and disease. For example, the unbranched beta-(1,3)-glucan can be derived from Euglena, can be chemically or mechanically modified, complexed with another chemical or trace metal, and/or can be part of other additives; e.g., pesticides, fertilizers, etc. The wellbeing of the plant or quality of the harvested plant material can be improved through the administration of unbranched beta-(1,3)-glucan, where "wellbeing" includes enhancement in one or more of the following aspects: growth rate, productivity of desired agricultural product (i.e. the crop), disease resistance, stress tolerance, reduced mortality rates, and improved immune function and where "quality of the harvested plant material" includes reduction in damage due to harvest, transport and storage, improvement in appearance, and longer shelf life.

The source of unbranched beta-(1,3)-glucan can be a non-toxic, nonpathogenic algae or protist of the genus Euglena. In certain aspects, a method of improving the immune function of any photosynthetic organism, be it a terrestrial or aquatic plant or its associated harvested tissues, is provided where the method includes administering to the plant or harvested tissues a composition comprising a beta glucan, where the beta glucan comprises unbranched beta-(1,3)-glucan. Unbranched beta-(1,3)-glucan can also be referred to as linear beta-(1,3)-glucan. The unbranched beta-(1,3)-glucan can be derived from Euglena and can be derived from heterotrophically grown Euglena. In some embodiments, the beta glucan in the composition can consist essentially of unbranched beta-(1,3)-glucan. In certain embodiments, the beta glucan in the composition can consist of unbranched beta-(1,3)-glucan. The beta glucan in the composition can also include greater than about 90% unbranched beta-(1,3)-glucan. The unbranched beta-(1,3)-glucan can be in the native form of paramylon, which is a water insoluble granule, or can be made water soluble through chemical or mechanical modifications.

The composition can further include a metal, such as iron, magnesium, lithium, zinc, copper, chromium, nickel, cobalt, vanadium, molybdenum, manganese, selenium, iodine, and combinations thereof. The unbranched beta-(1,3)-glucan and the metal can form a complex.

Administering the composition can include adding the composition in liquid form to the plant, either as a foliar spray directed towards the leaves, in liquid added to the ground near the plant (either alone on in combination with other liquids received by the plant, such as irrigation water, foliar sprays, liquid pesticides, liquid fertilizers, etc.), or added to the liquid in which the plant is growing (in the case of an aquatic organism or hydroponically grown plants). In addition, the beta glucan-containing composition can be added as a fine mist to any part of the plant or in a gel form that can be applied to any part of the plant or surrounding area, including sites of damage or wounds. The composition can also be applied as a dry powder, either to the plant itself or the surrounding area. The unbranched beta-(1,3)-glucan can be chemically or mechanically modified to be water-soluble or have other advantageous properties.

The present technology also demonstrates that unbranched beta-(1,3)-glucan can be produced at a low cost by using an algae or protist such as Euglena sp. using controlled growth methods. The structure of these beta glucans is different from the beta glucans produced using other organisms. One major difference is that while other organisms produce beta glucan incorporated into their cell wall, the genus of protists known as Euglena can produce beta glucan, including a particulate form of beta glucan, known as paramylon, which is not incorporated into the structure of the cell wall. Rather, Euglena accumulates beta glucan as a water-insoluble granule in the cytoplasm and utilizes this form of beta glucan as a form of carbohydrate energy storage. Under optimized growth conditions, it is possible to achieve concentrations of beta glucan where the net beta glucan weight is greater than 20% to 80% of the total dry weight proportion of the biomass. The present technology provides means to maximize Euglena growth while minimizing competing microorganism growth. The beta glucan compounds produced by Euglena are not the same as other products that are produced using yeast and other organisms, but the beta glucans from Euglena are effective at modulating immune function. The beta glucan produced from Euglena is predominantly unbranched beta-(1,3)-glucan. A further benefit is that beta glucan production cost can be less than ½ to ⅕ the production cost of beta glucans that are produced using yeast.

In other embodiments, the present technology includes a composition comprising an effective amount of beta glucan produced by an algae or protist such as Euglena, where the composition is used to improve the wellbeing of a plant or improve the quality of harvested plant materials. Lower-cost beta glucans produced using algae therefore provide affordable and natural alternatives to chemicals and genetic engineering for agriculturalists.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

DETAILED DESCRIPTION

Figure 1:
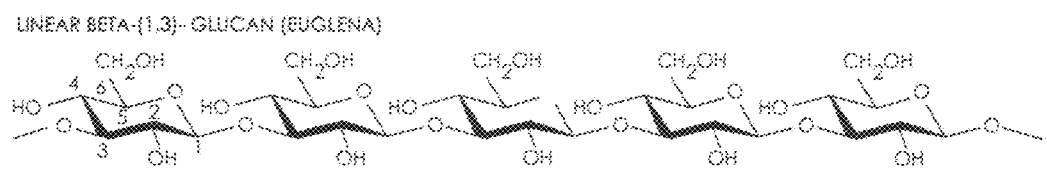
FIG. 1 illustrates a beta glucan derived from Euglena showing an unbranched beta-(1,3)-glucan structure.

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. Regarding the methods disclosed, the order of the steps presented is exemplary in nature, and thus, the order of the steps can be different in various embodiments. Except where otherwise expressly indicated, all numerical quantities in this description, including amounts of material or conditions of reaction and/or use are to be understood as modified by the word "about" in describing the broadest scope of the technology.

The present technology relates to beta glucan, including unbranched beta-(1,3)-glucan derived from *Euglena*, and uses thereof. Compositions containing *Euglena*-derived unbranched beta-(1,3)-glucan can be administered to a plant to modulate the immune function of the plant, where such modulation can promote immune system health, prevent disease, reduce mortality, reduce the effects of stress, increase growth rates, or improve crop productivity. Various agriculturally relevant products, such as cereal grains, oilseeds, fruits and vegetables, ornamental plants, flowers, etc., can be treated. Dosages or feed inclusion rates can vary depending upon the species that is administered the unbranched beta-(1,3)-glucan. Plants can also be treated at any stage of life. The present technology is intended to include compositions, use of the compositions, and various methods as described herein to enhance the wellbeing of photosynthetic organisms. Methods used to prepare such compositions are also included in the present technology.

Various uses and efficacies have been shown for beta glucans derived from yeast (e.g., U.S. Pat. No. 6,939,864), mushrooms (e.g., U.S. Pat. No. 5,147,821), and oats (e.g., U.S. Pub. No. 2011/0123677) for various applications, but there is less research on beta glucans derived from algae or protist sources. Beta glucans produced by an algae or a protist such as *Euglena gracilis* may be similar in some aspects to beta glucans from other sources, but algae and protist derived beta glucans are also unique in several ways. For one, *Euglena* produces unbranched beta-(1,3)-glucan. This type of beta glucan occurs as granules in the cytoplasm known as paramylon and can be more easily isolated and purified without the use of harmful solvents. With the technology disclosed herein, *Euglena* can be cost-effectively grown to contain a very high content of beta glucan that can be readily prepared into products for application to plants. The average molecular weight of beta glucans obtained from algae and protists can also be different from beta glucans from other sources, for example. For convenience, reference made herein to "beta glucan" that is prepared or derived from algae or protists (e.g., *Euglena*) is also understood to include unbranched beta-(1,3)-glucan.

Three-Dimensional Structure

The three-dimensional structure and folding of unbranched beta-(1,3)-glucan can affect the bioavailability, surface area, and overall efficacy in immune stimulation applications. In linear, unbranched beta-1,3-glucan chains, the structure is governed by the glycosidic linkage pattern. Because the chair-form ring of glucopyranosyl is rather rigid, most of the flexibility of the glucan chain arises from rotations around the bonds of the glycosidic linkages. X-ray crystallography and spectroscopy techniques indicate that linear glucans have a triple-helix backbone in the solid state. Paramylon that is produced by *Euglena* is considered to be one of the structurally most simple of the beta glucans, with few glycosyl side chains. An example structure of linear or unbranched beta-(1,3)-glucan from *Euglena* is shown in FIG. 1.

The structure of *Euglena*-derived beta glucan stands in contrast to laminaran, lentinan, scleroglucan, schizopylann, and yeast-derived beta glucans that have 1,4- or 1,6-linked side chains exposed toward the exterior of the helical structure. The triple-helix structure of unbranched beta-(1,3)-glucan is stabilized by three types of hydrogen bonding: (1) intermolecular hydrogen bonding formed between the different chains in the same x-y plane; (2) intramolecular hydrogen bonding formed between adjacent O atoms in the same chain; and (3) intermolecular hydrogen bonding formed between different chains in a different x-y plane. The triple helix structure is stable over a broad range of temperatures at a neutral pH, resulting in a polymer that is water insoluble. However, the hydrogen bonds can be destabilized by various means to change the conformation of the paramylon polymer. For example, paramylon can be dissolved in alkaline solutions (e.g., typically 0.2 M NaOH or stronger), aprotic polar solvents (e.g., DMSO), in the presence of strong chaotropic agents (e.g., urea), or by increasing temperatures above the triple-helix melting temperatures (e.g., ~135° C.).

Different immunological effects can be obtained that are related to the unbranched beta-(1,3)-glucan conformation, be it the native state, denatured, or denatured and re-natured. Unbranched beta-(1,3)-glucan in any of these three conformations can serve as the building block for additional reactions that add or improve its functionality. Several of these modifications can produce functionalized beta-(1,3)-glucans and some of their respective applications are discussed herein. The conformation of the beta glucan and its resulting solubility may also affect how it is delivered; for example, water soluble unbranched beta-(1,3)-glucan can be delivered via an aqueous carrier and particulate unbranched beta-(1,3)-glucan can be delivered as a solid or a dispersion.

Particle Size, Molecular Weight, and Surface Area

The particle size, molecular weight, and surface are all factors that affect the function and bioavailability of the beta-(1,3)-glucan particle. In certain aspects, it can be preferable to have a beta-(1,3)-glucan particle between 0.2 and 5 microns in diameter with a high surface area. Beta-(1,3)-glucans produced by Euglenoids can have a molecular weight of about 200-500 kDa, for example.

Sources of beta glucans, structures, and approximate molecular weights are shown below in TABLE 1.

TABLE 1

Sources of beta glucans, structures, and approximate molecular weights

| Name | Source | Native Form Solubility in Water | Structure | Approximate Molecular Weight (kDa) |
|---|---|---|---|---|
| Glucan from Euglenoids | Algae | Particulate | β-(1,3) unbranched | 200-500 |
| Glucan from Saccharomyces cerevisiae | Yeast | Particulate | β-(1,3)/β-(1,6) branched (30:1) | 200 |
| Curdlan | Gram negative bacteria | Particulate | β-(1,3) unbranched | 50-200 |
| Laminarin | Brown seaweeds | Soluble | β-(1,3) with some β-(1,6) branching (30:1). The β-(1,6) side chains are composed of two glucose units. | 7.7 |
| Scleroglucan | Fungus | Soluble | β-(1,3) β-(1,6) branched (6:1). The β-(1,6) side chains are composed of two glucose units. | 1020 |

Level of Purity of Beta-(1,3)-Glucan

The level of purity of a beta glucan compound can have an effect on efficacy, possibly stemming from other material present that affects the interaction between the beta glucan and plant cells. Using the methods described herein, paramylon can be isolated in the form of granules from Euglenoid cells. As a result, the purity of paramylon is high relative to preparations of beta glucans from yeast and other organisms. Using the methods described herein, purity levels greater than 99% (measured by an enzymatic assay which detects beta glucan, Megazyme) can be obtained. In comparison, the highest-grade yeast-derived beta glucans can rarely achieve greater than 90% purity and several commercial products in the animal feed industry specify only about a 35-60% purity. Moreover, preparing high purity beta-(1,3)-glucan can be achieved more cost-effectively than with yeast-derived glucans due to the ease of separation resulting from the lack of a cell wall in Euglenoids and easy recovery of paramylon granules. Finally, since no harsh chemicals (e.g., strong acids and bases) are required to recover the paramylon granules, the beta glucan can be recovered in its native form without modifying its chemical composition and configuration. In some cases, the use of pure, unmodified paramylon can be advantageous in comparison to solubilized and modified paramylon or beta glucans obtained from other organisms that are modified during the extraction process.

Method for Production of Paramylon in *Euglena* Gracilis

*Euglena* sp. may be grown in a controlled environment, such that the *Euglena* will remain the dominant microorganism in the environment. This is not easy to achieve, as other organisms are typically capable of competing for the same biological resources (e.g., nutrients, micronutrients, minerals, organic energy, and/or light). Many of these microorganisms typically have a faster growth rate and are capable of out-competing *Euglena* absent several controlled growth mechanisms that favor *Euglena* sp. These growth mechanisms can include one or more methods such as employment of growth media that favors *Euglena*, operation at a temperature that favors *Euglena*, addition of acids and bases that favor *Euglena*, addition of compounds that are toxic to competing organisms other than *Euglena*, selective filtration or separation of *Euglena*, and addition of micropredators or viruses that control the populations of organisms that are not *Euglena*. All of these methods can affect the growth rate and the ability of *Euglena* to produce beta glucan. In order to achieve a sufficient population of the algae or protist, the organism can be grown in large aerobic fermentation vessels that are optionally sterilizable.

The production of beta glucan may be enhanced by the addition of an organic carbon source to the *Euglena* growth media, by the selective addition of light, or by both. Again, these aspects affect the ability of *Euglena* to compete with other organisms. In general, *Euglena* that are grown in an uncontrolled environment will not display the same beneficial properties of high beta glucan concentration, fast growth rates, and efficient production of beta glucans that *Euglena* produced in a more controlled growth environment can display. The production of beta glucan using *Euglena* in a controlled environment such as a fermenter reduces the cost of beta glucan production in several ways, including the following: first, the beta glucan is not part of the cell wall of the organism and does not require elaborate and/or expensive fractionation methods or extraction processes; second, *Euglena* organisms are relatively large and may be separated from water relatively quickly by employing a centrifuge, filter, or other separation device; third, individual *Euglena* cells are composed of a larger percentage of beta glucan (as a percent of total cell mass) in comparison to other organisms, which results in high rates of conversion of organic sugars to beta glucan and easier recovery of the beta glucan; fourth, beta glucans produced from *Euglena* are structurally distinct from other beta glucans and have certain advantages.

The beta glucan can be provided as a suspension, paste, extract, or dry powder derived from *Euglena* sp., which has been grown heterotrophically in one or more sterile bioreactors. The *Euglena* can also be grown in an optimal manner such that the beta glucan portion of the algae biomass comprises greater than 20% of the algae biomass, as measured on a dry weight basis. Examples of processes for growing and creating such products are illustrated in FIGS. 2 and 3.

Figure 2:
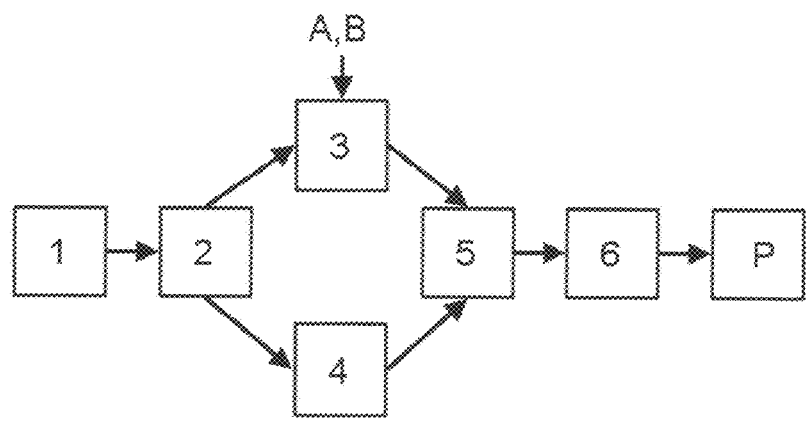
FIG. 2 is a schematic of an embodiment of a fermentation process according to the present technology.
Figure 3:
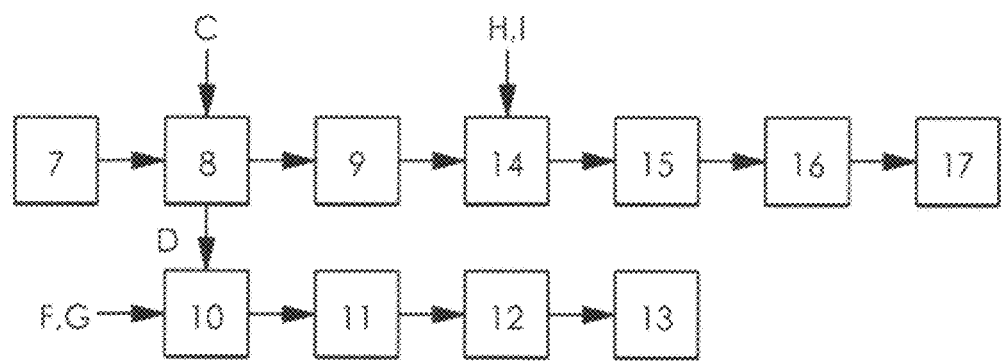
FIG. 3 is a schematic of another embodiment of a fermentation process according to the present technology.

With reference to FIG. 2, an embodiment of a fermentation process is shown. Algae biomass can be produced in a fermenter (1) under sterile conditions on chemically defined media. After the desired amount of time in the fermenter (1), the fermenter broth can be transferred to a centrifuge (2) that dewaters the broth to produce two process streams: a wet algae meal that contains about 75% moisture; and used media. Any dewatering device, such as a filter or membrane, could be used in place of the centrifuge. The wet algae meal contains a mixture of whole algae cells, algae cell fragments, and beta glucan granules. Prior to drying, the wet algae meal can optionally be transferred to a mixer (3), such as a mixing tank or any piece of equipment capable of mixing (e.g., ribbon blender), for additional processing. Examples of processing may optionally include the following: the pH of the wet algae meal can be adjusted by the addition of acid or base (A) in the mixer (3); a concentrated solution of a soluble metal salt (B), such as $ZnSO_4$—$H_2O$, can be added to the mixer (3) and mixed vigorously with the beta glucan solution for 1-120 minutes; the wet algae meal can be heated or cooled after centrifugation. Any water soluble metal salt (B) can be used. For example, the metal salt (B) can be mixed with the beta glucan so that the final product can be a copper beta glucan complex, zinc beta glucan complex, iron beta glucan complex, cobalt beta glucan complex, magnesium beta glucan complex, manganese beta glucan complex, and combinations thereof.

Preparation of the soluble metal salt (B) solution can involve heating a mixture of the metal salt (B) in water with mixing. Optionally, the mixer (3) can be heated or cooled. The mixer (3) can be heated to the temperature required to pasteurize the material and inactivate enzyme activity. When the beta glucan solution and metal salt (B) solution are mixing, some amount of complexation can occur between the metal ions and the beta glucan present in the wet algae meal such that the final product may be considered a metal-beta glucan complex.

In a further embodiment, the wet algae meal may be processed to isolate or extract the beta glucan; for example, by way of sonication, bead milling, or other means of mechanical disruption (4), or by contact with various chemicals (e.g., acids, bases, solvents, etc.) to dissolve or otherwise remove unwanted fractions of the wet algae meal prior to use. This process can optionally occur in the mixer (3). The beta glucan isolated from the cell biomass can be washed with water or a suitable alcohol (ethanol, isopropanol) to remove non-beta glucan materials. Additional washes can be performed with any chemical suitable to remove non-beta glucan materials. The pH of the beta glucan solution can be adjusted with acid or base if necessary.

After the desired amount of processing, the mixture can be transferred to a dehydrator (5), which can be any device capable of drying the material. For example, the dehydrator (4) can be a tray dryer, belt dryer, rotary drum dryer, spray dryer, etc. Once the material contains less than 10% moisture, it can optionally be transferred to a mill (6) where its particle size can be reduced to less than 1000 μm. More preferably, its particle size can be reduced to less than 250 μm. Once the material has been milled, it can be packaged (P) into containers of suitable size and labeled. Optionally, the addition of the metal salt (B) solution to the wet algae meal can be omitted and the resultant product will be algae meal or fractions of algae meal.

With reference to FIG. 3, another embodiment of a fermentation process is shown. Algae biomass is produced in a fermenter (7) under sterile conditions on chemically defined media. Algal biomass can also be produced in a growth tank under non-sterile conditions using any media that contains only feed-grade materials and is free of harmful substances (e.g., heavy metals, toxins, dangerous chemicals). After the desired amount of time in the fermenter or growth tank (7), the fermenter broth can be transferred to a mixer (8), such as a mixing tank or any piece of equipment capable of providing mixing (e.g., ribbon blender). If so equipped, the fermenter can serve as the mixer. The fermenter broth contains a mixture of whole algae cells, algae cell fragments, and beta glucan granules. In the case of a non-sterile growth tank, low levels of non-algal biomass can also be present. Optionally, the pH of the fermenter broth can be adjusted by addition of acid or base chemicals (C) to the mixer (8) to lyse cells, thereby releasing the majority of the beta glucan granules from within the cells. For example, this can be accomplished by adding base (e.g., NaOH) to the fermenter broth. The broth can also be processed mechanically through a high-pressure homogenizer or ultrasonic cell disruptor to lyse cells or any means well known to those well versed in the art of fermentation.

It should be appreciated that the use of homogenizers can create a well distributed beta glucan solution. For example, where *Euglena* is first grown in the fermenter and then centrifuged, the beta glucan can be extracted from the *Euglena* and dried to a powder. The base chemicals can then be used to dissolve the powder, followed by a precipitation of a clear gel through the addition of acid to form a base-disrupted beta glucan. The base-disrupted beta glucan gel is at least partly soluble in water at a neutral pH, and at low concentrations (e.g., 100 ppm) has been found to disperse well into an aqueous solution. When the gel has been washed, for example, it can be suspended in water using a homogenizer to obtain an emulsion, or an otherwise well-mixed aqueous solution. The homogenized beta glucan solution may then be bottled for transportation and end use.

The broth can be adjusted to an alkaline pH and then neutralized prior to centrifugation. After sufficient time where most if not all cells are lysed, the resultant mixture is transferred to a centrifuge (9) that dewaters the broth to produce two process streams: a crude beta glucan solution (D); and mixture of other biomass materials (E). The crude beta glucan solution (D) can be transferred to a mixer (10), such as a mixing tank or any piece of equipment capable of providing mixing (e.g., ribbon blender). The crude beta glucan solution (D) can be washed with water or a suitable alcohol (ethanol, isopropanol) to remove non-beta glucan materials. Additional washes can be performed with any chemical suitable to remove non-beta glucan materials. The pH of the crude beta glucan solution (D) can be adjusted with acid or base (F). A concentrated solution of a soluble metal salt (G), such as $ZnSO_4$—$H_2O$, can be prepared and added to the mixing tank (10) and mixed vigorously with the beta glucan solution for 1-120 minutes. Any water-soluble metal salt can be used, such that the final product can be, for example, a copper beta glucan complex, zinc beta glucan complex, iron beta glucan complex, cobalt beta glucan complex, magnesium beta glucan complex or manganese beta glucan complex. Preparation of the soluble metal salt solution may involve heating a mixture of the metal salt in water with mixing. Optionally, mixer (10) may be heated or cooled. The mixer (10) can be heated to the temperature required to pasteurize the material and inactivate enzyme activity. When the beta glucan solution and metal salt solution are mixing, some amount of complexation can occur between the metal ions and the beta glucan present such that the final product can be considered a metal-beta glucan complex. Optionally, the addition of the metal salt (G) solution to the wet beta glucan material can be omitted and the resultant product will be pure beta glucan.

After the desired amount of mixing, the mixture can be transferred to a dehydrator (11), which is any device capable of drying the material. For example, the dehydrator (11) can be a tray dryer, belt dryer, rotary drum dryer, spray dryer, etc.

Once the material contains less than 10% moisture, it can be optionally be transferred to a mill (12) where its particle size can be reduced to less than 500 µm. More preferably, its particle size can be reduced to less than 250 µm. One the material is milled, it is packaged (13) into bags of suitable size and labeled. The non-beta glucan material (E) contains partially hydrolyzed proteins and amino acids and can be transferred to a mixer (14), such as mixing tank or any piece of equipment capable of providing mixing (e.g., ribbon blender). The pH of the non-beta glucan material (E) may optionally be adjusted with acid or base (H). A concentrated solution of a soluble metal salt (I), such as $ZnSO_4—H_2O$ can be prepared and added to the mixer (14) and mixed vigorously with the amino acid-rich material for 1-120 minutes. Any water-soluble metal salt can be used, such that the final product can be, for example, a copper proteinate, zinc proteinate, iron proteinate, cobalt proteinate, magnesium proteinate, manganese proteinate, and combinations thereof. Preparation of the soluble metal salt solution can involve heating a mixture of the metal salt in water with mixing. Optionally, mixer (14) may be heated or cooled. The mixer (14) can be heated to a temperature required to pasteurize the material and inactivate enzyme activity. When the non-beta glucan solution and metal salt solution are mixing, some amount of complexation can occur between the metal ions and the partially hydrolyzed proteins and amino acids present such that the final product can be considered a metal proteinate. Optionally, the addition of the metal salt solution (I) to the non-beta glucan material € can be omitted and the resultant product will be extracted algae meal.

After the desired amount of mixing, the mixture can be transferred to a dehydrator (15), which is any device capable of drying the material. For example, the dehydrator (15) may be a tray dryer, belt dryer, rotary drum drier, multi-effect evaporator, etc. Once the material contains less than 10% moisture, it can optionally be transferred to a mill (16) where its particle size is reduced to less than 500 µm. More preferably, its particle size can be reduced to less than 250 µm. Once the material is milled, it can be packaged (17) into bags of suitable size and labeled.

Optionally, the addition of the metal salt solution to each process stream (D, E) can be omitted and the resultant products will be a relatively pure beta glucan and partially hydrolyzed protein meal. Advantages to complexing the trace metal and the beta glucan include an increase in the bioavailability of the trace metal in combination with the immune system modulating aspects of beta glucan. The beta glucan can protect or shield the trace metal from binding to an agonist, for example. Furthermore, because some trace elements, such as zinc, may be important in obtaining optimal immune system functionality, the combination with an immune enhancing compound such as beta glucan can be more preferable in some situations.

Optionally, the purified wet beta glucan (D) can we stored, packaged, and used in the wet state without requiring any drying. It can optionally be further processed to improve the efficacy of the beta glucan.

Methods of Modifying Beta Glucans from *Euglena* sp.

Products containing beta glucan, including purified beta glucan produced as described above, may undergo additional reactions in order to improve its functionality. For example, reactions that can be used to alter the structure of the beta glucan compound in order to increase or alter the efficacy of immune system stimulation include (but are not limited to): sulfation, phosphorylation, acetylation, and amination.

Simple procedures to lyse the *Euglena* cells and concentrate the beta glucan can achieve a product that can exceed 95% purity of beta glucan. This isolated product has the benefit of being more concentrated, having lower protein content to reduce unwanted side reactions, and also permits a longer shelf life. This isolated product can be administered to a plant by itself or in conjunction with another material or process, such as a fertilizer, pesticide, during irrigation, crop harvesting, and/or crop packaging practices.

Methods of Modifying Beta Glucan Chain Length

In order to achieve different or desirable properties, it may be beneficial to alter the beta glucan chain length using enzymes, catalysts, heat, sonication, or combinations thereof. Additionally, it can be beneficial to start with a highly pure linear source of beta glucan, such as beta glucans derived from *Euglena gracilis*, in order to achieve a desired range of optimal target chain lengths.

One non-limiting example of a process for achieving a beta glucan with a shorter chain length includes the following steps.

1. Start with beta glucan derived from *Euglena* having an average molecular weight of 500 kDa. Glucose is about 140 Daltons, so 500 kDa represents a linear chain of approximately 3,000-4,000 glucose subunits
2. Optionally, a pre-preparation of the beta glucan may be required to unwind or unzip the crystalline beta glucan structure that occurs in paramylon derived from *Euglena*.
3. Cleave the molecule, where one example of a target molecular weight includes approximately 5 to 20 kDa, or approximately 30 to 250 glycosidic subunits. In some cases it may be beneficial to cleave the molecule prior to unwinding or unzipping the 3D structure of the beta glucan chain such as to expose only a portion of the bonds between glycosidic subunits. Cleavage techniques can include:
    a. Enzymatic cleavage, such as by using beta glucanase or a similar enzyme.
    b. Ultrasonification, either on a plate or by combining with ultrasonified micro-particles or nano-particles.
    c. Use of a catalyst.
    d. Heat.
    e. Use of energy-transferring wavelengths emitted from a device such that the waves are absorbed by the bonds linking the subunits, where sufficient energy is applied to break a portion of the bonds.
4. An optional separation or purification step can be performed where a relatively homogeneous product is desired and the resulting chain lengths of the cleaved beta glucan are not uniform. Size selection of beta glucan can include:
    a. Centrifugation or sedimentation, where heavier molecules are more dense, have less relative surface area.
    b. Filtration, e.g. using Millapore-type or other filter or a series of such filters, to separate or isolate the target beta glucan chain-length.
    c. Chromatography, such as size-exclusion chromatography.
    d. Electrophoresis, including gel electrophoresis.

Methods of Modifying Beta Glucan Solubility

Solubility of the beta glucan can be modified using various techniques in order to administer the beta glucan using an aqueous vehicle. Application of heat is one method to increase the solubility. For example, an amount of beta glucan ranging from 0.1% to 10% (as measured by mass) can be combined with boiling water or other aqueous solution for at least 10 minutes and cooled to room temperature. The result is a solubilized beta glucan solution having a viscosity related to the amount of beta glucan. The viscosity can be tailored based upon the resulting chain length and/or the concentration of the beta glucan. For example, it is possible to heat beta glucan in an aqueous solution to provide a viscosity of about 600 g/cm$^2$ or more for certain applications. Such solutions can have a gel-like consistency.

Combinations of *Euglena*-Derived Beta Glucans with Other Substances

In some embodiments, *Euglena*-derived beta glucans can be used in combination with one or more other types of beta glucans (e.g., yeast derived beta glucans) in order to provide immune modulation properties. The *Euglena*-derived beta glucans can also be combined with various other substances for administration to a plant. Examples of such other substances include one or more of the following: fertilizer, pesticide, herbicide, corn meal, dehulled soybean meal, wheat middlings, limestone, monocalcium-dicalcium phosphate, salt, manganous oxide, manganese sulfate, zinc oxide, ferrous sulfate, copper sulfate, cobalt carbonate, calcium iodate, sodium selenite, vitamin A, vitamin D, vitamin E, Menadioane sodium bisulfate complex (source of vitamin K complex), riboflavin supplement, niacin supplement, calcium pantothenate, vitamin B12, d-biotin, thiamine mononitrate, pyridoxine hydrochloride, folic acid, methionine, soybean oil, mineral oil, amino acids, chicken meal, bone meal, calcium, phosphorus, chrondrotin, glucosamine, Omega 3 & Omega 6, beet pulp, DHA (from fish oil), beta carotene, fish meal, vitamin blend, alpha-linlenic acid, amino acids, arachidonic acid, ascorbic acid, beef meal, biotin, brewers yeast (dried), calcium carbonate, cellulose, chelated minerals, chondroitin sulfate, cobalt, copper, corn oil, dicalcium phosphate, DL-methionine, docosahexaenoic acid, dried egg product, durum flour, ethoxyquin, fat, carbohydrates, ferrous sulfate, fiber, fish meal, fish oil, flax meal, folic acid, fructooligosaccharides, gelatin, glucosamine hydrochloride, glycerin, ground barley, ground corn, ground sorghum, guar gum, inositol, iodine, iron, lamb meal, I-carnitine, linoleic acid, lutein, magnesium, magnesium oxide, manganese, marigold extract, mannanoligosaccharides, minerals, mixed tocopherols, monosodium phosphate, niacin, marigold extract, blueberries, dried kelp, phosphorus, potassium, potassium chloride, potassium iodide, potassium sorbate, protein, pyridoxine hydrochloride, riboflavin, rice, rice flour, rosemary, rosemary extract, tapioca starch, taurine, thiamine mononitrate, titanium dioxide, vitamin A, vitamin B-1, vitamin B12, vitamin B-2, vitamin B-6, vitamin C, vitamin D3, vitamin E, vitamin K, water, wheat, wheat glutens, xanthan gum, zinc, zinc oxide, zinc sulfate, any of the ingredients presently listed by the Association of American Feed Control Officials, and combinations thereof. Further ingredients can be included for enhancing immune system activity: vitamin C, alfalfa, flax seed, parsley, cranberries, spirulina, chlorella, vitamin A, vitamin E, copper, zinc, chromium, iron, arginine, alklyglcerol, coenzyme Q10, dimethglycine, phytonutrients, beta carotene, essential oils, fish oils, spices and their derivatives, and combinations thereof. The ingredients above may be used in various applications and for stimulating the immune system of plants.

The composition including the beta glucan can also be formulated as a concentrate which is sufficiently storage stable for commercial use and which is diluted, for example with water, before use. Alternatively, each component the composition can be formulated as a separate concentrate for mixing and dilution prior to use. Compositions include liquid compositions, which are ready for immediate use, and solid or liquid concentrated compositions, which require dilution with a solvent before use, typically water.

Solid compositions including beta glucan can be in the form of granules or dusting powders wherein the active ingredient is mixed with a finely divided solid diluent (e.g., kaolin, bentonite, kieselguhr, dolomite, calcium carbonate, talc, powdered magnesia, Fuller's earth, or gypsum). Solid compositions can also be in the form of dispersible powders or grains, and can include a wetting agent to facilitate the dispersion of the powder or grains in a liquid. Solid compositions in the form of a powder may be applied as foliar dusts.

Liquid compositions can comprise a solution, suspension or dispersion of the beta glucan in water and can also contain a surface-active agent, or can comprise a solution or dispersion of the beta glucan in a water-immiscible organic solvent which is dispersed as droplets in an aqueous solution. The composition can contain additional surface active agents, including for example surface active agents to increase the compatibility or stability of concentrated compositions as discussed above. Such surface-active agents can be of the cationic, anionic, or non-ionic or amphoteric type or mixtures thereof. Cationic agents include, for example, quaternary ammonium compounds (e.g., cetyltrimethylammonium bromide). Examples of anionic agents include soaps, salts of aliphatic mono esters of sulphuric acid, for example sodium lauryl sulphate; and salts of sulphonated aromatic compounds, for example sodium dodecylbenzenesulphonate, sodium, calcium, and ammonium lignosulphonate, butylnaphthalene sulphonate and a mixture of the sodium salts of diisopropyl and triisopropylnaphthalenesulphonic acid. Suitable non-ionic agents are the condensation products of ethylene oxide with fatty alcohols such as oleyl alcohol and cetyl alcohol, or with alkylphenols such as octyl- or nonylphenol or octylcresol. Other non-ionic agents are the partial esters derived from long chain fatty acids and hexitol anhydrides, for example sorbitan monolaurate; the condensation products of the partial ester with ethylene oxide; the lecithins; and silicone surface active agents (water soluble of dispersible surface active agents having a skeleton which comprises a siloxane chain e.g. Silwet L77™). A suitable mixture in mineral oil is ATPLUS 411F™.

The present compositions can further include various compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like. The compositions can also contain other components, for example, herbicides, plant growth regulators, fungicides, insecticides, and the like, and can be formulated with liquid fertilizers or solid, particulate fertilizer carriers such as ammonium nitrate, urea, and the like.

The composition including beta glucan and further contain a surfactant, where the surfactant lowers the surface tension of a liquid, allowing easier spreading. The surfactant can be a detergent, an emulsifier (including alkyl polyglucosides glycerol ester or polyoxyethylene (20) sorbitan monolaurate), a dispersing agent (including sodium chloride, potassium chloride, potassium nitrate, calcium chloride or starch of corn), a foaming agent (including derivates of tartric acid, malic acid or alcohols), a penetration enhancer, a humectant (including ammonium sulfate, glycerin or urea) or a wetting agent of ionic or non-ionic type or a mixture of such surfactants. Various types of surfactants include penetration enhancers, dispersing agents or emulsifiers.

Penetration enhancers include compounds that accelerate the uptake of beta glucan through the cuticle of a plant into the plant, i.e. the rate of uptake, and/or increases the amount of beta glucan absorbed into the plant. Various types of substances known as penetration enhancers include alkyl phosphates, such as tributyl phosphate and tripropyl phosphate, and naphthalenesulphonic acid salts. Examples of penetration enhancers include those sold under the trade name Dehscofix™, comprising castor oil and ethoxylated fatty acids, such as Dehscofix CO 95™ (available from Huntsman, USA), comprising C18 ethoxylated fatty acids from castor oil.

Dispersing agents can be added to a suspension including the beta glucan, usually a colloid, to improve the separation of particles and to prevent settling or clumping. Examples of such dispersing agents include products available under the trade name Tensiofix Dp400 (available from Ajinomoto OmniChem), essentially comprising organic sulfonate and 2-methylpentane-2,4-diol.

Emulsifiers can be added to stabilizes an emulsion including the beta glucan, i.e. a mixture of two or more liquids. Examples include those available under the trade names Tween™ 20, which includes polyoxyethylene (20) sorbitan monolaurate (polysorbate 20), and Radia™, which essentially comprises alkyl polyglycosides.

Additional examples of various surfactants include one or more of the following: castor oil ethoxylate, rapeseed methyl estr, alkyl phosphates, tributyl phosphate, tripropyl phosphate, naphthalenesulphonic acid salts, organic sulfonate/2-methylpentane-2,4-diol, alkylpolyglucoside, siloxanes derivates, alkylsulfonates, polycarboxylates lignosulfonates, alkoxylated triglycerides, fatty amines polymers, dioctylsulfosuccinates or polyoxyethylene (20) sorbitan monolaurate (polysorbate 20), more preferably said surfactant is C18-castor-oil-ethoxylate (Dehscofix™), organic sulfonate/2-methylpentane-2,4-diol (Tensiofix Dp40) or polyoxyethylene (20) sorbitan monolaurate (Tween™20).

Combinations of *Euglena*-Derived Beta Glucans with Fungicides and Bactericides

Beta glucan may be combined in a composition with other compounds known to prevent pathogenesis in plants, such as a fungicide and/or a bactericide. Fungicide refers to a chemical or biological substance or composition used to kill or inhibit fungi or oomycetes, e.g. by preventing sporulation, or their spores. Fungicides can exert their biological effect by different modes of action, for example, by interference with nucleic acid synthesis, mitosis and cell division, respiration, amino acids and protein synthesis, signal transduction, lipids and membrane synthesis, sterol biosynthesis, glucan synthesis in the pathogen or by inducing host plant defense. Such compositions may be provided as a powder, spray or even dissolved in the water supply and provided through a form of irrigation. Examples of natural fungicides that may be combined with beta glucan include tea tree oil, cinnamaldehyde, cinnamon essential oil, jojoba oil, neem oil, rosemary oil, monocerin, milk, ampelomyces sp., *Bacillus* sp., *Ulocladium* sp., powdered kelp, and combinations thereof. Examples of other fungicides that may be combined with beta glucan include phosphonates, benzamides, carbamates, dithiocarbamates, phtalimides, triazoles, quinolines, sulphur, cyanoimidazoles, and combinations thereof. Still further examples of fungicides include acylalanines (benalaxyl), anilinopyrimidines (cyprodinil or pyrimethanil), benzamides (fluopicolide or zoxamide), benzimidazoles (fuberidazole, thiabendazole or metrafenone), benzothiadiazoles (acibenzolar-S-methyl), carbamates (benthiavalicarb, iprovalicarb or propamocarb), carboxamides (boscalid), chloronitriles (chlorothalonil), chlorophenyls (tolclophosmethyl), cyanoacetamide oximes (cymoxanil), cyanoimidazoles (cyazofamid), dicarboximides (iprodione), dithiocarbamates (thiram, metiram, mancozeb, manebe or propineb), guanidines (dodine), hydroxyanilides (fenhexamid), imidazoles (fenamidone, imazalil or triflumizole), morpholines (dimethomorph, fenpropimorph, spiroxamine or dodemorph), phosphonates (fosetyl), oxathiins (flutolanil), oxazoles (famoxadone or hymexazol), phenylamides (metalaxyl or metalaxy-M), phenylpyridinamides (fluazinam), phenylpyrroles (fludioxonil), phtalimides (captan or folpet), quinazolinones (proquinazide), quinolins (quinoxyfen), strobilurins (dimoxystrobin, fluoxastrobin, kresominmethyl, pyraclostrobin, trifloxystrobin or picoxystrobin), thiophenes (silthiofam), triazoles (difenoconazole, epoxyconazole, fenbuconazole, flusilazole, metconazole, myclobutanil, penconazole, propiconazole, tebuconazole, tetraconazole, triadimenol, triticonazole or prothioconazole), copper derivates (copper oxychloride, copper hydrochloride, copper oxide or copper sulphate), sulphur, and combinations thereof.

The present compositions can further comprise one or more plant immune system modulators, such as silica, copper, sulfur, aluminium, vanadium, cobalt, nickel, iron, silver, salicylic acid and its derivates (including acetylsalicylic acid, isonicotinic acid, acibenzolar-S-methyl), jasmonic acid and its derivates (including methyl jasmonate), ethylene and its derivates, polysaccharides (including glucans, xyloglucans, chitin, chitosans, fucans, galactofucans, xylans, galactans, alginates, galacturonans, apiogalacturonans, fructans including inulin, mannans, xylomannans, galactomannans, glucomannans and galactomannans), algae extracts (green algae extracts including ulvans, brown algae extracts including laminarin, and red algae extracts including carragenans), oligosaccharides (including trehalose), peptides (including systemin, 13-pep, flg-22, glutathion), amino acids, proteins (including harpin and flagellin), peptone, beef extract, essential oils (including cumin, anise, mint, cinnamon, thyme, basil, cardamom, coriander, oregano, manzanilla, clove, jojoba and tea tree oils), lipids (including ergosterol, amphotericin, sphingolipids, cerebrosides), glycolipids (including syringolids), glycoproteins (including cryptogeins), lipopeptides, lipoproteins (including volicitin), yeast extracts (including extracts from *Saccharomyces, Candida, Pichia, Aureobasidium* and more particularly *Saccharomyces cerevisiae, Candida famata, Candida oleophila, Pichia guilliermondii, Aureobasidium pullulans*), fungal extracts (including extracts from *Trichoderma, Megasperma, Pyricularia, Alternaria, Pythium, Puccinia, Colletotrichum, Verticillium, Magna porthe*), bacterial extracts (including extracts from *Escherichia, Rhyzobia, Pseudomonas*), BABA, probenazole, isothianil, phosphorous acid and its derivates (including aluminium, sodium and potassium fosetyl), horsetail extracts, potassium iodide and potassium thiocyanate, Citrus extracts, Yucca extracts, Salix extracts, and plant decoctions (including nettle decoction).

The various compositions including beta glucan can also be combined or coadministered with bacteriophages or bacteriocides in order to provide an additional level of protection to the plant.

All-Natural Compositions

In certain embodiments, an all-natural *Euglena*-derived beta glucan composition may be desirable, such as for use in organic farming applications that typically require pesticide-free and/or synthetic chemical-free certifications. In this case, the beta glucan can provide an all-natural source of immune support for a plant. Additionally, the beta glucan can be provided as algae meal or a partially fractionated or partially purified algae meal where, in addition to beta glucan, the algae meal provides a natural source of various macronutrients such as nitrogen, phosphorus, potassium, sulfur and also a number of other valuable micronutrients or trace metals. The composition including the beta glucan can be produced to meet organic standards, such as those required for organic certification and accreditation by the United States Department of Agriculture; see the National Organic Program available online at [www.ams.usda.gov]. For example, an all-natural *Euglena*-derived beta glucan composition can be prepared without the use of irradiation, sewage sludge, synthetic fertilizers, prohibited pesticides, and genetically modified organisms.

Such all-natural compositions may be developed that are more potent due to the addition of beta glucan as a PAMP. One or more of the following ingredients may be combined with beta glucans in order to achieve a desired immune stimulation effect: probiotics (*Bacillus* sp., specifically QST 713 strain of *Bacillus subtillus*), cod liver oil, plant derived oils (corn oil, cottonseed oil, garlic oil, clove oil, neem oil), essential oils (thyme, basil, oregano, rosemary). These substances may be dissolved or mixed with inert ingredients such as water, lauric acid, polyglycerols, or other substances.

Administration to Plants

The various compositions including beta glucan described herein can be administered to a plant in various ways. The rate of administration of the composition of the present invention can depend on a number of factors including, for example, the active ingredients, the plant species, the growth stage and density of the plant species, the formulation and the method of application, as for example, spraying, addition to irrigation water or other conventional means. In some embodiments, the administration can be from 10 to 1000 liters of composition per hectare, where certain embodiments include using 100 to 200 liters of composition per hectare.

Administration of the composition can be carried out in accordance with techniques well known to persons skilled in the art. The composition can be applied to the whole plant, or to leaves, flowers, fruits, seeds and/or roots of the plant, as well as to the soil or inert substrate wherein the plant is growing or in which it is desired to grow (e.g. inorganic substrates like sand, rockwool, glasswool; expanded minerals like perlite, vermiculite, zeolite or expanded clay), pumice, pyroclastic materials or stuff, synthetic organic substrates (e.g. polyurethane), organic substrates (e.g. peat, composts, tree waste products like coir, wood fiber or chips, tree bark) or to a liquid substrate (e.g. floating hydroponic systems, Nutrient Film Technique, Aeroponics). The application can be done by spraying, drenching, soaking, dipping, injection, etc., or via irrigation systems. It can also be useful to apply the composition to propagation material such as tubers or rhizomes, as well as seeds, seedlings, or seedlings pricking out and plants or plants pricking out. The compositions can also be applied post-harvest to control decay. For example, the composition can be applied to harvested crops or plant material, including fruits, vegetables, cereal grains, tubers, etc.

It can be beneficial to provide the beta glucan composition in a way that maximizes absorption of beta glucan to a plant. For example, younger or wetter plant leaves can be more receptive to absorption of beta glucan. It can also be beneficial to provide beta glucan at a certain time. For example, plant respiratory metabolic pathways can be more active during selective exposure to the appropriate combinations of light, humidity, temperature, soil moisture, nutrient loading, or other conditions. In particular, application to CAM or C4 plants may be more beneficial during the night or when the plants are exposed to moist conditions. It can also be possible to provide a hormone or other cellular signal with beta glucan in order to promote the plant to receive beta glucans for a limited period of time.

For certain applications, beta glucan can be modified or formulated as a gel. This can have the benefit of providing moisture and stability to a plant cutting, root, or hydroponically grown plant with reduced evaporation. For example, cuttings or portions of plants used for asexual propagation can be treated with the compositions described herein. Such compositions, including those formulated as gels, can also help to facilitate the transmission of plant hormones, such as a rooting hormone, either by ensuring that the hormone maintains close physical proximity to the plant or by providing insulation from variations in temperature that may degrade the hormone or to prevent the hormone from evaporating.

Beta glucan can also be applied hydroponically to plants, such as to stimulate the immune system of roots, stems, cuttings, or cultivars. This may be particularly beneficial to plants that are being cloned from specific genetic strains of plants, such as is often intentioned by plant breeders. Beta glucan can also be administered in the form of an algae meal, where dry algae meal is used or where the algae meal is liquefied and fed to the plant. For example, liquefied whole-cell algae paste, which, in addition to providing a source of immune stimulant, also has the benefit of providing a rich source of nutrients and micronutrients to the plant.

EXAMPLES

Beta Glucan Branching Analysis

The beta glucan produced by Euglenoids is unique in its physical characteristics and is often referred to as "paramylon." Paramylon consists of a linear polymer that is almost exclusively unbranched beta-(1,3)-glucan having very few, if any, side branches. This structure differs significantly from the yeast-derived beta glucans that have been studied most intensively and commercialized for immune support applications. Yeast beta glucans contain a beta-(1,3)-glucan backbone that is substituted with beta-(1,6) side chains (2-3 glucose units long) every 10-30 glucose units. The unbranched nature of paramylon is an important distinction compared to other sources of beta glucans when considering its use in immune support applications. After isolating paramylon from whole *Euglena* cells, a linkage analysis was performed to determine the relative amounts of each type of bond between glucose monomers.

For glycosyl linkage analysis, the sample was permethylated, depolymerized, reduced, and acetylated, and the resulting partially methylated alditol acetates (PMAAs) were analyzed by gas chromatography-mass spectrometry (GC-MS) as described by York et al. (1985) Methods Enzymol. 118:3-40. Initially, dry sample was suspended in about 300 µl of dimethyl sulfoxide and placed on a magnetic stirrer for 1-2 weeks. The sample was then permethylated by the method of Ciukanu and Kerek (1984) Carbohydr. Res. 131:209-217 (treatment with sodium hydroxide and methyl iodide in dry DMSO). The sample was subjected to the NaOH base for 10 minutes then methyl iodide was added and left for 40 minutes. The base was then added for 10 minutes and finally more methyl iodide was added for 40 minutes. This addition of more methyl iodide and NaOH base was to insure complete methylation of the polymer. Following sample workup, the permethylated material was hydrolyzed using 2 M trifluoroacetic acid (2 h in sealed tube at 121 C), reduced with NaBD$_4$, and acetylated using acetic anhydride/trifluoroacetic acid. The resulting PMAAs were analyzed on a Hewlett Packard 5975C GC interfaced to a 7890A MSD (mass selective detector, electron impact ionization mode); separation was performed on a 30 m Supelco 2330 bonded phase fused silica capillary column.

A linkage analysis of two paramylon samples extracted from *Euglena gracilis* is shown below in TABLE 2.

TABLE 2 linkage analysis of two paramlyon samples extracted from *Euglena gracilis*

| GLYCOSYL RESIDUE | Sample 1 | Sample 2 |
| --- | --- | --- |
| terminally-linked glucopyranosyl residue (t-glc) | 0.34 | 0.3 |
| 3-linked glucopyranosyl residue (3-glc) | 93.03 | 94.1 |
| 4-linked glucopyranosyl residue (4-glc) | 2.25 | 2.4 |
| 2,3-linked glucopyranosyl residue (2,3-glc) | 3.47 | 2.3 |
| 3,6-linked glucopyranosyl residue (3,6-glc) | 0.36 | 0.8 |
| 2,3,4-linked glucopyranosyl residue (2,3,4-glc) | 0.55 | 0.1 |
| Total | 100.0 | 100.0 |

The linkage analysis indicates that both paramylon samples are mainly composed of 3-linked glucopyranosyl residues. For example, the beta glucan can be greater than about 90% unbranched beta-(1,3)-glucan, and in some cases can be greater than about 93% unbranched beta-(1,3)-glucan or greater than about 94% unbranched beta-(1,3)-glucan. Minor amounts of 4-linked and 2,3 linked glucopyranosyl residues were found along with negligible amounts of 3,6-linked, terminal and 2,3,4-linked glucopyranosyl residues. These data confirm that paramylon is comprised mostly of linear, unbranched beta-(1,3)-glucan. Beta-(1,3)-glucan is the form of beta glucan believed to bind to receptors on the surface of immune system cells of mammals, such as Dectin-1 (a major receptor on immune system cells like macrophages) and complement receptor 3. It is possible that beta-(1,3)-glucan interacts with plants in a similar fashion.

Plant Experiments:

Preparation of beta glucan solution: 1 M NaOH was prepared by dissolving 12 g NaOH in 0.3 L distilled H2O. Finely ground unbranched beta-1,3-glucan powder (1 g) was added to 0.1 L of 1 M NaOH and briefly stirred at room temperature. The solubilized beta glucan was then precipitated by slow addition, with periodic stirring, of HCl until the pH was neutral. The neutralized slurry was transferred to 50 mL conical tubes and centrifuged to remove salt. The supernatant was discarded, the tubes were filled to the 50 mL mark with distilled H2O, mixed by briefly vortexing, and centrifuged again. This wash step was repeated a total of three times. The washed 1% (10,000 ppm) gel was diluted to a final concentration of 0.01% (100 ppm) by adding 10 mL of the gel to a volumetric flask and filling to the 1 L mark with distilled water. This 100 ppm solution was used in the following experiments.

Experiment 1: Effect of Beta Glucan Preparation on Plant Disease

Methods: Cucumber plants (variety SMR 58) were treated with a foliar spray when the first true leaf of the cucumber was ⅔ fully expanded. Plants were sprayed with either the beta glucan preparation or distilled water. One week after spraying, 20 sites on each leaf were each inoculated with a 5 µl droplet of fungal spores (concentration was 100,000 spores/ml) of the plant pathogen *Colletotrichum orbiculare*. One week after inoculation, plants were scored for disease by counting lesions, as shown in TABLE 3.

TABLE 3

LESION COUNTS

| Treatment | Mean Lesions (#/leaf) |
| --- | --- |
| Beta glucan solution | 5.8 ± 3.7 |
| Water | 19.6 ± 0.5 |

The beta glucan solution significantly reduced the number of pathogenic lesions which developed on each leaf compared to the control. This demonstrates that application of the beta glucan solution to plant leaves can reduce susceptibility to plant diseases.

Experiment 2: Effect of Beta Glucan Preparation on Plant Disease

Methods: Cucumber plants (variety SMR 58) were treated with a foliar spray when the first true leaf of the cucumber was ⅔ fully expanded. Plants were sprayed with either the beta glucan preparation or distilled water. One week after spraying, 10 sites on each leaf were each inoculated with a 5 µl droplet of fungal spores (concentration was 100,000 spores/ml) of the plant pathogen *Colletotrichum orbiculare*. One week after inoculation, plants were scored for disease by measuring lesion diameter, as shown in TABLE 4.

TABLE 4

LESION DIAMETER

| Treatment | Lesion Area (mm$^2$) |
| --- | --- |
| Beta glucan solution | 7.45 ± 4.19 |
| Water | 12.53 ± 7.65 |

The beta glucan solution appeared to reduce the size of pathogenic lesions which developed on each leaf compared to the control. This demonstrates that application of the beta glucan solution to plant leaves can reduce susceptibility to plant diseases.

Experiment 3: Effect of Beta Glucan Preparation on Development of Dry Rot of Potato Caused by *Fusarium sambucinum*.

Figure 4:
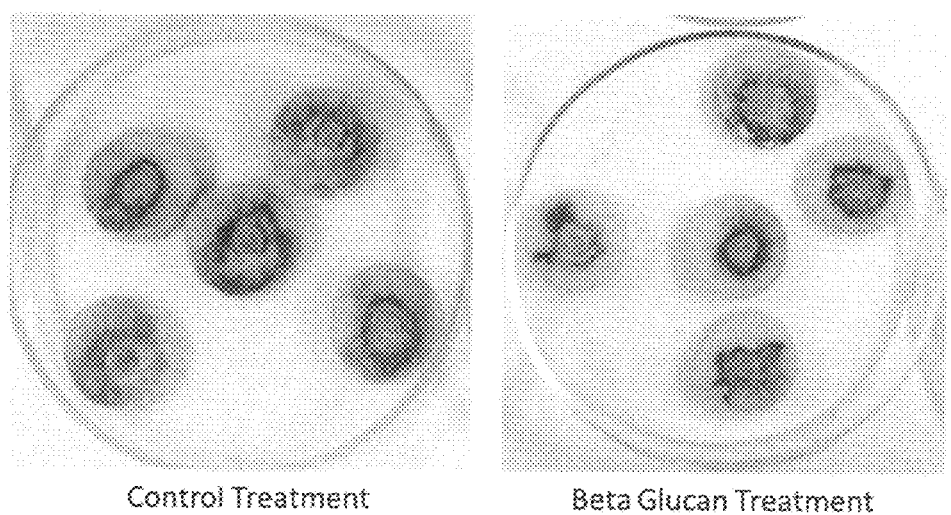
FIG. 4 is a depiction of potato tuber disks treated with a beta glucan solution (experimental) relative to potato tuber disks treated with distilled water (control), the experimental and control disks shown one week after the respective treatments.

Method: Tuber disks (2 cm diameter by 0.5 cm thick) were prepared from the central cortex tissue for potato tubers (variety Snowden). The disks were rinsed 3 times with sterile water and then treated by soaking for 3 minutes in beta glucan solution or distilled water. The disks were placed onto sterile filter paper in petri dishes and allowed to sit for 2 days. After 2 days, the disks were inoculated with a plug of mycelium from a culture of *F. sambucinum*. The photograph shown in FIG. 4 was taken one week after the initial treatment (5 days after inoculation).

It is evident that the tuber discs treated with the beta glucan solution are less infected five days after introduction to the fungus. This demonstrates that application of the beta glucan solution to harvested plant materials like potato tubers can improve the quality of plant products by reducing their susceptibility to disease.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms, and that neither should be construed to limit the scope of the disclosure. In some example embodiments, well-known processes, well-known device structures, and well-known technologies are not described in detail. Equivalent changes, modifications and variations of some embodiments, materials, compositions and methods can be made within the scope of the present technology, with substantially similar results.

What is claimed is:

1. A method of modulating the immune function of a plant, the method comprising administering to the plant a composition comprising beta glucan derived from *Euglena*, the beta glucan comprising unbranched beta-(1,3)-glucan, said beta-(1,3)-glucan having a molecular weight of at least 200,000 Daltons.

2. The method of claim 1, wherein the *Euglena* is heterotrophically grown.

3. The method of claim 1, wherein the beta glucan consists essentially of unbranched beta-(1,3)-glucan.

4. The method of claim 1, wherein the beta glucan consists of unbranched beta-(1,3)-glucan.

5. The method of claim 1, wherein the beta glucan comprises greater than about 90% unbranched beta-(1,3)-glucan.

6. The method of claim 1, wherein the beta glucan comprises paramylon.

7. The method of claim 1, wherein the composition further comprises algae meal.

8. The method of claim 1, wherein the composition is a liquid composition.

9. The method of claim 1, wherein the composition is a gel composition.

10. The method of claim 1, wherein the composition further comprises a member selected from the group consisting of a fertilizer, a pesticide, a fungicide, a bactericide, and combinations thereof.

11. The method of claim 1, wherein the composition further comprises a plant immune system modulator other than beta glucan.

12. The method of claim 1, wherein the composition further comprises a surfactant.

13. The method of claim 12, wherein the surfactant is selected from the group consisting of a penetration enhancer, a dispersing agent, and an emulsifier.

14. The method of claim 1, wherein the administering comprises contacting a surface of the plant with the composition.

15. The method of claim 1, wherein the administering comprises contacting a substrate in which the plant is growing with the composition.

16. The method of claim 1, wherein the administering comprises irrigating the plant with water and the composition.

17. The method of claim 1, wherein the plant is a seed or a seedling.

18. The method of claim 1, wherein the plant is a harvested plant product.

19. The method of claim 18, wherein the harvested plant product is selected from the group consisting of a fruit, a vegetable, a cereal grain, and a tuber.

20. The method of claim 1, wherein the plant is a cutting or a portion of a plant being asexually propagated.

21. The method of claim 1, wherein the plant is being grown hydroponically or aeroponically.

22. The method of claim 1, wherein the composition is prepared without the use of irradiation, sewage sludge, synthetic fertilizers, synthetic pesticides, and genetically modified organisms.

23. The method of claim 1, wherein the unbranched beta-(1,3)-glucan has an average molecular weight less than the native average molecular weight of unbranched beta-(1,3)-glucan derived from *Euglena*.

24. The method of claim 23, wherein the average molecular weight of the unbranched beta-(1,3)-glucan is modified by a method selected from the group consisting of ultrasonification, enzymatic cleavage, chemical reaction, contact with a catalyst, selective filtration selective chromatography, selective centrifugation, heating, radiation, and combinations thereof.

25. A method of modulating the immune function of a plant, the method comprising: administering to the plant a composition comprising beta glucan derived from *Euglena*, the beta glucan comprising unbranched beta-(1,3)-glucan, wherein the beta glucan is at least partially complexed with a water-soluble metal salt to provide a metal-beta glucan complex, said beta-(1,3)-glucan having a molecular weight of at least 200,000 Daltons.

26. The method of claim 1 wherein the composition further comprises a metal.

27. The method of claim 26 wherein the metal comprises a member selected from the group consisting of iron, magnesium, lithium, zinc, copper, chromium, nickel, cobalt, vanadium, molybdenum, manganese, selenium, and combinations thereof.

28. The method of claim 26, wherein the beta glucan and the metal form a complex.

29. A method of modulating the immune function of a plant, the method comprising: administering to the plant a composition comprising beta glucan derived from *Euglena*, the beta glucan comprising unbranched beta-(1,3)-glucan, said beta-(1,3)-glucan having a molecular weight of at least 200,000 Daltons, wherein the beta glucan is at least partially complexed with a water-soluble metal salt to provide a metal-beta glucan complex, said water-soluble metal salt selected from the group consisting of one or more of a copper proteinate, a zinc proteinate, an iron proteinate, a cobalt proteinate, a magnesium proteinate, and a manganese proteinate.

* * * * *